(12) United States Patent
Hardwick et al.

(10) Patent No.: US 11,085,926 B2
(45) Date of Patent: Aug. 10, 2021

(54) METHODS OF SCREENING

(71) Applicant: Phoremost Limited, Cambridge (GB)

(72) Inventors: Bryn Shaun Hardwick, Cambridge (GB); Grahame James McKenzie, Cambridge (GB)

(73) Assignee: Phoremost Limited, Cambridge (GB)

( * ) Notice: Subject to any disclaimer, the term of this patent is extended or adjusted under 35 U.S.C. 154(b) by 0 days.

(21) Appl. No.: 16/064,283

(22) PCT Filed: Dec. 22, 2016

(86) PCT No.: PCT/GB2016/054038
§ 371 (c)(1),
(2) Date: Jun. 20, 2018

(87) PCT Pub. No.: WO2017/109499
PCT Pub. Date: Jun. 29, 2017

(65) Prior Publication Data
US 2019/0004058 A1 Jan. 3, 2019

(30) Foreign Application Priority Data
Dec. 22, 2015 (GB) ...................................... 1522618

(51) Int. Cl.
*G01N 33/68* (2006.01)
*G16B 20/00* (2019.01)
*G16C 20/50* (2019.01)

(52) U.S. Cl.
CPC .......... *G01N 33/6845* (2013.01); *G01N 33/68* (2013.01); *G01N 33/6842* (2013.01); *G16B 20/00* (2019.02); *G16C 20/50* (2019.02); *G01N 2500/10* (2013.01); *G01N 2800/7028* (2013.01)

(58) Field of Classification Search
None
See application file for complete search history.

(56) References Cited

U.S. PATENT DOCUMENTS

| 2003/0215846 A1 | 11/2003 | Watt et al. |
| 2007/0031832 A1 | 2/2007 | Watt et al. |
| 2007/0128657 A1 | 6/2007 | El-Gewely |
| 2009/0028889 A1 | 1/2009 | Nakaar et al. |
| 2010/0305002 A1 | 12/2010 | Chenchik et al. |

FOREIGN PATENT DOCUMENTS

| EP | 2210944 A1 | 7/2010 |
| WO | 0186297 A2 | 11/2001 |
| WO | WO 2004/042074 A2 | 5/2004 |
| WO | WO 2010/040073 A1 | 4/2010 |
| WO | WO 2010/129310 A1 | 11/2010 |
| WO | 2013116903 A1 | 8/2013 |
| WO | 2015095355 A2 | 6/2015 |

OTHER PUBLICATIONS

Atke et al (European Journal of Pharmacology 271:63-8) (Year: 1995).*
Pruitt et al (Genome Research 19:1316-23). (Year: 2009).*
Watt Nat Biotech 24: 177-183 (Year: 2006).*
Chattopadhay et al. "A peptide aptamer to antagonize BCL-6 function", Oncogene, vol. 25, Dec. 5, 2005, pp. 2223-2233.
Koehbach et al. "Oxytocic plant cyclotides as templates for peptide G protein-coupled receptor ligand design", Proceedings National Academy of Sciences PNAS, vol. 110, No. 52, Nov. 18, 2013, pp. 21183-21188.
Fujii et al. "Peptides Inhibitory for the Transcriptional Regulatory Function of Human Papillomavirus E2", Clinical Cancer Research, Nov. 1, 2003, pp. 5423-5428.
International Search Report in PCT/GB2016/054038 dated May 9, 2017 (5 pages).
Chu, Q. et al., "Discovery and Characterization of a Novel Class of Functional Polypeptides," *Crit. Rev. Biochem. Mol. Biol.*, vol. 50, pp. 134-141 (2015).
Madaule, P. et al., "A peptide library expressed in yeast reveals new major epitopes from human immunodeficiency virus type 1," *FEMS Microbiology Immunology*, vol. 76, pp. 99-108 (1991).

* cited by examiner

*Primary Examiner* — Christopher M Gross
(74) *Attorney, Agent, or Firm* — Bookoff McAndrews, PLLC

(57) ABSTRACT

The invention provides a method of identifying a peptide interaction site on a target protein wherein the target protein modulates the phenotype of a mammalian cell, using mammalian encoded peptides (SEPs) such as short open reading frame (sORF) encoded peptides. The invention further provides a method for the identification of new therapeutic targets and protein interaction sites for use in drug discovery.

19 Claims, 6 Drawing Sheets

METHODS OF SCREENING

CROSS-REFERENCE TO RELATED APPLICATIONS

This application is the U.S. national phase entry under 35 U.S.C. § 371 of International Application No. PCT/GB2016/054038, filed on Dec. 22, 2016, which claims benefit of priority to GB Application No. 1522618.6, filed on Dec. 22, 2015.

FIELD OF THE INVENTION

This invention relates to methods for the identification of new therapeutic targets and novel druggable protein interaction sites for use in drug discovery.

BACKGROUND OF THE INVENTION

The identification of new therapeutic targets is a key starting point for drug discovery. Drug discovery efforts have traditionally been focused upon identifying classically-druggable targets, such as kinases, G-protein coupled receptors (GPCRs) and ion channels. However, such chemically facile targets do not always represent the most biologically relevant targets for therapeutic intervention. Drugging protein:protein interactions (PPIs) is of particular interest because these represent the predominant type of target involved in defective signaling pathways utilised by cancer cells and a large set of potentially actionable interfaces in human disease. Unfortunately, systematic attempts to drug PPIs and other 'undruggable' targets have been limited by technological restrictions, in large part due to limitations in current high-throughput DNA and RNA-based genomics technologies in being able to identify new druggable space at the proteome level.

Current genomics-based technologies that can identify candidate drug targets linked to disease biology using unbiased 'phenotypic' assays, have typically been performed using gene knock-outs (e.g., CRISPR), or at the transcriptomic level using RNAi. These approaches yield important information on which targets may represent important nodes in disease progression and therapeutic intervention in disease, but suffer a serious limitation: because they screen at the genetic, rather than protein-level, they cannot identify how to drug those targets or determine if those represent druggable candidates as an inherent part of the process. This is because such genetic screens remove target proteins rather than inhibiting them. To gain such crucial additional information on druggability, a new high-throughput proteome-level screening technology would need to be used; one that can handle the higher complexity of screening protein function (>300,000 unique protein transcripts and millions of unique PPIs) compared to gene function (~30,000 genes and their splice variants).

Recently, the systematic identification of novel drug target sites directly in the human proteome has gained a level of tractability and attention with the introduction of DNA-encoded, protein-fragment expression libraries, that can be screened in high throughput in phenotypic assays (such as described in WO 2013/116903); often dubbed 'Protein-interference' (Protein-i). Such protein-fragment libraries, typically derived from diverse bacterial genomes, are composed of small self-folding sub-domains that form the evolutionary building blocks of larger proteins. When assembled into libraries for intracellular expression in mammalian cells, they represent a highly diverse collection of 3-dimensional shapes for docking to target proteins and exploring candidate novel druggable sites across the human proteome. Crucially, these protein fragments are small enough to describe discrete spatial sites in target proteins, and thus can be recapitulated with small-molecule drugs subsequently designed to match that shape. Moreover, because protein-fragment libraries describe many more shapes than current small-molecule libraries, this offers a more robust approach to informing the rational design of future small molecule drugs to novel validated targets.

While bacterial-derived protein-fragment libraries have been shown to be effective in Protein-i screening and are highly efficient/straightforward to generate by fragmenting and cloning into expression libraries due to bacterial genomes being composed mostly of coding sequence. They may, however, be under-powered in possessing a large fraction of protein-fragments that can functionally interact with mammalian (e.g. human) proteins, compared to using fragments of a mammalian or human proteome itself.

However, creating protein-fragment libraries directly from a mammalian (e.g. human) genome is complicated by the fact that higher organisms have a much larger number of coding sequences and thus generally require a large degree of manual bespoke cloning to assemble fragments thereof into expression libraries for phenotypic screening. This is because the DNA of higher organisms contains mostly non-coding sequences (>95% of human DNA is estimated to be non-coding) and a much larger absolute number of coding sequences. They therefore require a unique and distinct approach to assemble fragments thereof into expression libraries for phenotypic screening.

Those bacterial-derived protein-fragment libraries described to date (e.g. in WO2013/116903) are obtained by mechanically shearing genomes and randomly inserting fragments into vectors. This leads to many fragments of random size that are either in frame (1:6 chance) or out of frame (5:6 chance) with the original gene in the bacterium. The same strategy would not work for eukaryotic organisms since most of their DNA is non-coding. In addition, bacterial-derived protein-fragment libraries such as these have no "inventory" i.e. because the sequences were randomly cloned it is not possible to say exactly what is contained within a given library other than by very deep sequencing.

These practical limitations have led to significant inertia in mining a potentially rich alternative vein of directly relevant protein-fold structural diversity in target-identification and validation screens in human cells.

Other screening approaches are described, for example, in WO 01/86297. Here random short (40-mer and 20-mer) peptide phage display libraries are generated and used to find peptides that bind to a pre-selected target or a known, pre-identified consensus motif. This relies on existing disease targets being known/recognised and does not facilitate the identification of new targets.

Accordingly, it is an object of the present invention to provide a method of screening a library of mammalian proteins and/or protein fragments.

SUMMARY OF THE INVENTION

In one aspect, the invention provides a method of identifying a target protein that modulates the phenotype of a mammalian cell, said method comprising exposing a population of in vitro cultured mammalian cells capable of displaying said phenotype to a library of SEPs ("short expressed peptides"); identifying in said cell population an alteration in said phenotype following said exposure, selection of said cells undergoing the phenotypic change and identifying a SEP that alters the phenotype of the cell, providing said SEP and identifying the cellular protein that binds to said SEP, said cellular protein being a target protein that modulates the phenotype of the mammalian cell.

"SEPs" are "short expressed peptides" derived from a library of DNA coding sequences. SEPs are short peptides (<150 amino acids). In preferred embodiments, a SEP is a peptide of 6 to 130 amino acids, preferably 6 to 100 amino acids. Such a peptide may be up to 20, 30, 40, 45, 46, 50, 60 or more amino acids. For example, such a peptide may of 6 to 45 amino acids or 6 to 60, 6 to 70, 6 to 80, 6 to 90 or 60 to 100 amino acids. In one embodiment, a SEP is a peptide of 40 or more amino acids, preferably 40 to 60 amino acids. SEPs are encoded by fragments of nucleotide sequence. As used herein, the term "SEP" may refer to the peptide or amino acid sequence, or to the nucleic acid sequence encoding for said peptide/amino acid sequence. In one embodiment, SEPs are mammalian, suitably human. They represent an untapped reservoir of biologically functional peptides for defining potential novel functional druggable targets in the human genome.

In one embodiment of any aspect of the invention, a "library of SEPs" can include peptides encoded by nucleic acid molecules from a single species, organism or individual or from mixed origins. Advantageously, a "library of SEPs" is a from a single organism, preferably mammalian, e.g. human. The "library of SEPs" can refer to a library of peptides or to a library of nucleic acid molecules encoding said peptides. In one embodiment of any aspect of the invention, the library of SEPs comprises peptides derived from mammalian, e.g. human, nucleic acid sequences.

Advantageously, the library of SEPs in accordance with the invention is in-silico designed to only use expressed proteins from a proteome consensus database. In addition, in one embodiment, the SEPs in the library are of constant size (which is an advantage in library generation/cloning and in the next generation sequencing (NGS) analysis/screening). Suitably, therefore, the library comprises SEPs of 6 to 100 amino acids (or nucleic acid molecules encoding the same), preferably SEPs of 40 or 45 to 100 amino acids. Moreover, a human library in accordance with the invention is designed to be in frame (no premature stops due to frameshifts) and the peptides expressed match to a human protein 100% of the time. A human library in accordance with the invention is, furthermore, spaced across all proteins in the human proteome and is present in a complete inventory since fragments are generated by massively parallel synthesis rather than a random cloning process.

In another embodiment, the library may also further include peptides from a microorganism and/or peptides from a small genome of a eukaryotic species. In one embodiment, the library may include peptides encoded by a bacterial-derived library (see, for example, WO 2013/116903 and citations referred to therein) in combination with sequences from non-bacterial sequences e.g. mammalian-derived sequences.

To generate a SEP library and prioritise those sequences, particularly human sequences, most likely to be biologically relevant within a constrained fragment size, one could search for and exploit either naturally short expressed functional sequences in the human genome, or rationally select fragments from larger proteins based on current bioinformatic predictions of domain structures.

With respect to the former approach, a new class of small (typically <100 amino acids), expressed, and evolutionarily-conserved protein-coding sequences have recently been identified in genomes such as the human genome. These sequences are called 'short open reading frames' (sORFs) and given their evolutionary conservation from bacteria to humans, are likely to encode functional peptides (or micropeptides). Identification of sORFs is reviewed, for example, by Chu et al., Critical Reviews in Biochemistry and Molecular Biology Volume 50, Issue 2, pages 134-141, 2015.

In one embodiment SEPs include peptides encoded by natural short open reading frame (sORF) sequences. Such sORF sequences may be derived from any organism. In one embodiment, sORFs are from mammalian nucleic acid, suitably human nucleic acid.

Describing the putative functions of sORFs is still at an immature stage, but some have now been shown to possess biologically relevant activities; often achieving large regulatory outputs by altering the intrinsic properties of other larger proteins (a potentially attractive feature in trying to identify novel druggable sites in PPI targets). For example, a sORF identified in Drosophila called 'Polished Rice' has been shown to substantially modify the activity of a much larger repressive transcription factor called 'Shaven Baby' (Chu Q et al, Critical Reviews in Biochemistry and Molecular Biology, 2015, 50(2), 134-141). 'Polished Rice' acts by recruiting and guiding the normally non-selective protein-degradation (proteasome) machinery to specifically cleave Shaven Baby into a truncated form that is now a transcriptional activator, rather than a suppressor. Such a major change elicited in a common and important class of 'undruggable' PPI target, if systematically harboured by many other sORFs, could represent a rich source for designing novel small molecule inhibitors of PPIs.

With improvements in genome annotation algorithms, many more sORFs are now being shown to exist. Their previous obscurity lies in the fact that they are often expressed as 'passengers' within larger conventional gene structures, or possess unconventional promoter regions and/or translational start codons when occurring as stand-alone genes. Currently 2000 predicted candidate sORFs have been described, with many of these being shown to be expressed, but as yet most have not been ascribed a function.

Thus, in one embodiment, SEPs include the peptide products of sORFs, such as natural sORFs found in the human genome. Suitably, the library of SEPs comprises a library of expressed sORFs. Such a library may comprise 2000 or more different putative sORFs. The method of the present invention provides a live cell assay system which enables large libraries such as these to be screened in a high throughput manner.

In another aspect or embodiment, a SEP library may include rationally selected fragments from larger proteins based on current bioinformatic predictions of domain structures i.e. bespoke cloned pre-defined subdomains of human and/or mammalian peptides, or micropeptides (e.g. human subdomain libraries). Suitably selected fragments will have self-folding potential and are chosen for maximum shape diversity. Such bespoke cloning may be achieved by e.g. DNA synthesis or a PCR method using primers which recognise a particular sequence characteristic of a sequence encoding a molecule with a particular function e.g. signaling receptor, transcription factor etc.

In another aspect or embodiment, a SEP library may be comprised of peptides encoded by a randomly cloned cDNA library e.g. by shot-gun cloning. Methods for random cloning are described herein.

In another aspect or embodiment, a SEP library may be comprised of peptides encoded by fragments coming from in silico designed short sequences based on available expressed protein databases. Methods for such designs are described herein.

The invention also relates to the generation of a sORF library, preferably a whole "sORFome" library (i.e. representing all naturally expressed sORFs), and screening the resultant peptide library of sORFs or a combined library of sORFs with other SEPs (e.g. "SEPome library") to identify one or more SEPs that modulate disease-associated pathways. These methods may be useful in identifying and characterising novel druggable target proteins and also protein:protein interaction (PPI) or allosteric sites for use as drug targets for the modulation of these pathways.

The advantage provided by the invention described herein is that it allows the full complexity of the "sORFome" and/or "SEPome library" and/or a large scale SEP library to be screened for its function in a live cell 'phenotypic' assay format. This method permits strong positive selection and the isolation of a small number of true hit peptides from a very large number of non-hit peptide sequences, suitably enabling a clear linkage with disease to be established.

The identification of SEPs and their target proteins, including their druggable binding sites, can be directly linked to disease, represented as a disease-model, in a precise, efficient and reliable manner and offers clear advantages in the development of suitable drug candidates for the treatment of disease.

In particular, the method of the invention provides for the identification of key novel druggable sites that play a role in disease progression that may not otherwise be identifiable.

The advantage of screening SEP libraries is that they, like small molecule drugs, act by directly and acutely inhibiting (or activating) target function (rather than eliminating the target's long-term expression). In screening for pathway suppressors, which is often the case in cancer research, the key to this method is turning a 'negative' cell phenotype signal (e.g., shut down of a signaling pathway or disruption of a protein/protein interaction) into a positive signal that can be selected for, or isolated from a large pool of cells harbouring inactive peptide sequences.

Advantageously, in one embodiment, the methods in accordance with the present invention do not screen to identify interactions with known targets or molecules comprising similar consensus sequences but rather screen for phenotype. This enables the present method to test and/or identify many hundreds of thousands of gene products as potential targets. The present invention allows a method for detecting naturally occurring binding without the use of random libraries and the construction of motifs.

Although the invention is predominantly focused on the use of human SEP (including sORF) libraries and human subdomain libraries to generate and identify SEPs and thereby novel druggable targets, novel aspects of the invention may be derived from cDNA-derived SEP libraries from lower-organism, non-human sources, such as shotgun cloned cDNA-derived libraries. For example, sequences may be obtained from the proteomes of bacteria, viruses and parasites known to cause human diseases. These are of interest in respect of those organisms known to cause disease by disrupting particular cellular processes. Particularly interesting are also bacteria constituting the gut flora, many of which are known to be involved in the process of mucosal immunity. cDNA-derived SEPs from such organisms are expected to elicit immunomodulatory effects on cells of the immune system, and therefore might find utility in the treatment of autoimmune disorders. In general, if a cellular process has been identified for cDNA-derived SEP libraries, it is possible to identify phenotypic effects using assays which measure such processes. Thus it is possible to couple bespoke cDNA-derived SEP libraries with bespoke, knowledge-led phenotypic assays.

In one embodiment, there is provided a method according to any aspect of the invention wherein the cellular protein and the SEP are used in an assay to identify ligands that bind to said cellular protein and disrupt SEP binding e.g. disrupt binding of said SEP to said cellular protein.

Advantageously, in the methods in accordance with the invention, there is no requirement for there to be an identified candidate target prior to screening.

In another aspect, there is provided a method of identifying a compound which binds to a target protein and displaces or blocks binding of said SEP wherein the compound modulates the phenotype of a mammalian cell, said method comprising the steps:
  i. exposing a population of in vitro cultured mammalian cells capable of displaying said phenotype to a library of SEPs;
  ii. identifying a cell in the population that displays an alteration in said phenotype following said exposure;
  iii. identifying a SEP that alters said phenotype of the cell;
  iv. identifying a cellular protein that binds to said SEP, said cellular protein being a target protein that modulates said phenotype of the mammalian cell;
  v. identifying a compound that binds to said target protein and displaces or blocks binding of said SEP.

In one embodiment, the phenotype of a mammalian cell is one associated with a disease-associated pathway. Suitable disease-associated pathways include an activated cell signaling pathway; and/or one selected from the list consisting of: differentiation, transcriptional activity, protein expression, resistance to infection, permeability and proliferation.

In one embodiment, said library of SEPs comprises (i) a plurality of separate and addressable SEPs; or (ii) said library of SEPs is expressed from a plurality of separate or addressable nucleic acids that encode SEPs.

In one embodiment, (i) said library of SEPs comprises a pooled plurality of SEPs or (ii) said library of SEPs is expressed from a pooled plurality of nucleic acids that encode SEPs.

In another aspect there is provided a library of SEPs as described herein. In one embodiment, there is provided a library of SEPs as described in the Examples section herein.

In one embodiment, said diseased cells are selected from cancer cells, autoreactive T-cells, inflamed cartilage cells and insulin-resistant cells.

In another embodiment, said diseased cells are selected from primary/patient derived cells and/or induced pluripotent stem cells.

In another aspect there is provided a library of SEPs comprising (i) a plurality of separate and addressable SEPs; or (ii) a plurality of separate or addressable nucleic acids that encode SEPs. In one embodiment, the library of SEPs comprises a plurality of sORFs.

In another aspect there is provided a use of a SEP identified in a method in accordance with the invention in a screening method for identifying a compound which interacts with said SEP.

In another aspect there is provided a SEP identified in a method in accordance with any aspect of embodiment of the invention for use as a medicament. In another aspect there is provided a method of treatment of a disease in a subject in need thereof comprising administering to said subject a therapeutically effective amount of a SEP identified in a method in accordance with the invention.

FIGURES

Figure 5:
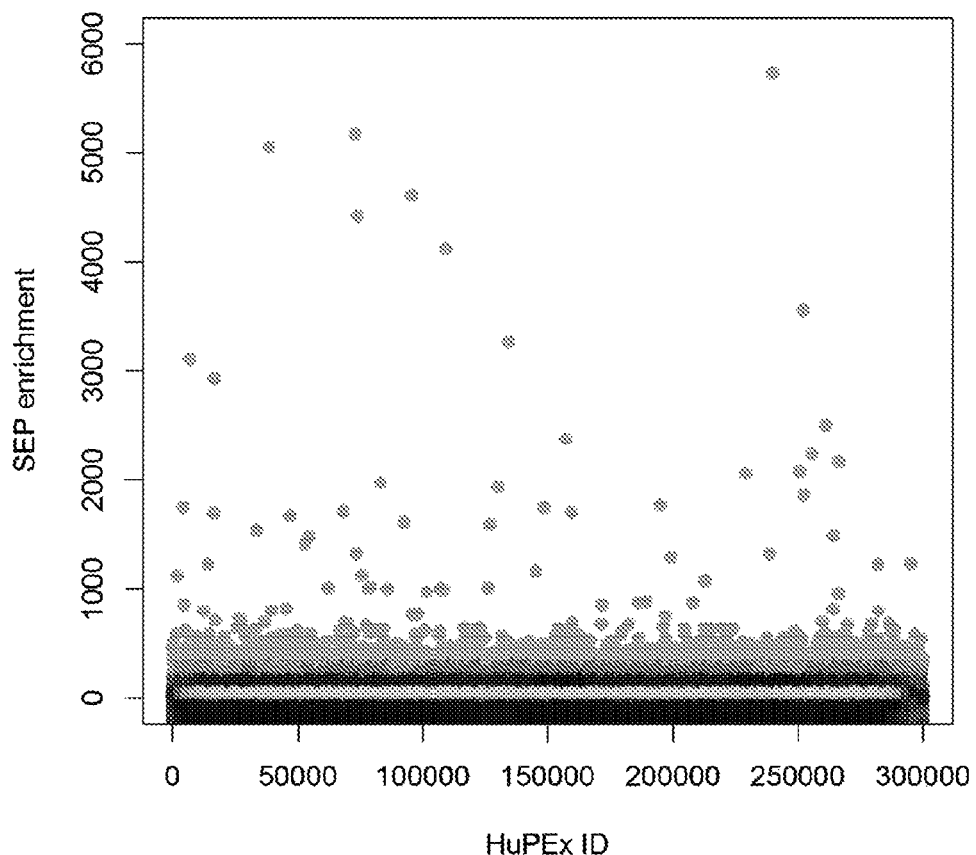

FIG. 5 shows a screen for SEPs able to overcome 6-TG toxicity. Cells carrying a library of SEPs are treated with 500 nM 6-TG for 6 days. Enrichment between 6-TG treatment (n=3) and DMSO control (n=3) is shown.

Figure 6:
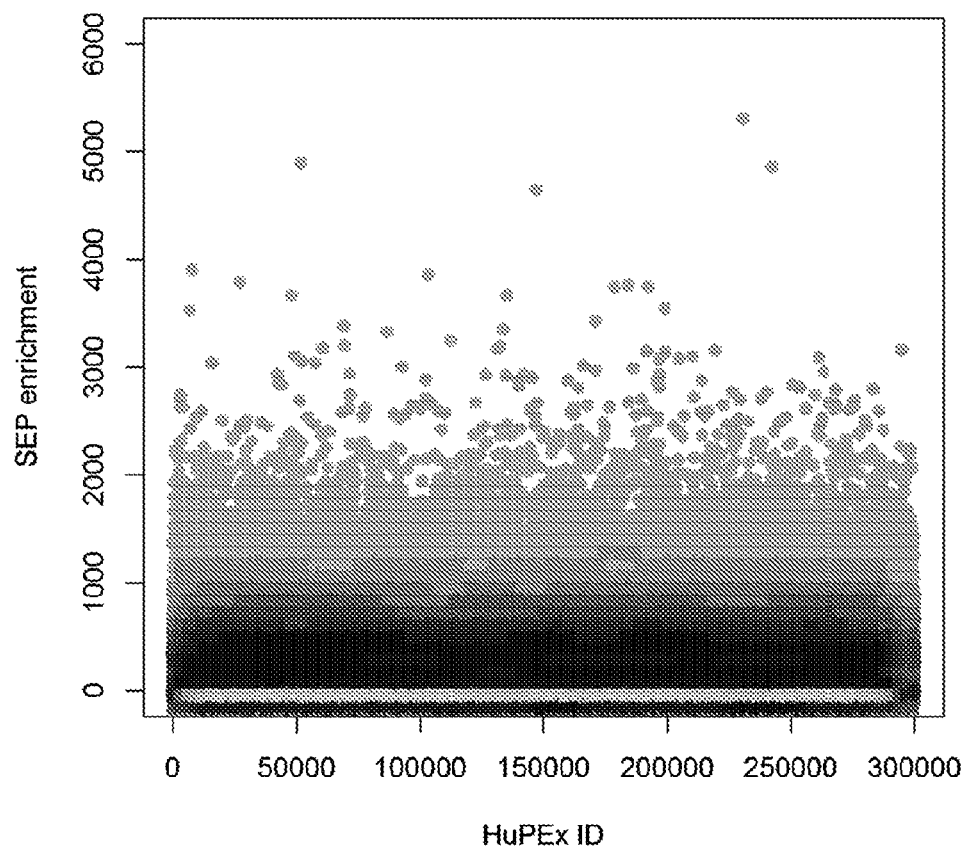

FIG. 6 shows a screen for SEPs able to down-regulate YAP signaling. Cells carrying a library of SEPs and a construct containing a YAP-response element linked to a GFP reporter are sorted in a YAP/GFP low and basal YAP/GFP population. Fold enrichment of Low YAP SEPs over a baseline YAP signal is shown.

DETAILED DESCRIPTION OF INVENTION

SEPs are preferably derived from cDNA sequences. The nucleic acid encoding the SEP from one or more transfected or transduced cells may be amplified, cloned and/or sequenced. The nucleic acid encoding the SEP may be expressed to produce the SEP.

In some embodiments, a cell or cell population may be transfected or transduced with a nucleic acid encoding SEP or a library of nucleic acids encoding a diverse population of SEPs, respectively.

Nucleic acid used to generate SEPs may include genomic DNA, RNA or cDNA obtained from one or more different organisms, preferably human or mammalian species. In one embodiment, SEPs are generated from a mixture of different organisms which may include prokaryotes. In one embodiment, SEPs are encoded by short open reading frames (sORF) of around 100 codons, from human and/or other mammalian sources. SEP libraries may be constructed using any convenient technique.

In another embodiment, SEPs may be constructed by cloning short fragments of nucleotide sequence from one or more mammalian nucleic acids into expression vectors. In one embodiment, SEPs may be constructed by randomly cloning short fragments of nucleotide sequence from one or more mammalian nucleic acids into expression vectors. Suitable methods for fragment generation include, for example, mechanical shearing (e.g. by sonication or passing the nucleic acid through a fine gauge needle), digestion with a nuclease (e.g. DNase 1), digestion with one or more restriction enzymes, preferably frequent cutting enzymes that recognize 4-base restriction enzyme sites, and treating the DNA samples with radiation (e.g. gamma radiation or ultra-violet radiation). In one embodiment, fragments may be generated through bioinformatics based design of fragments followed by DNA synthesis. In some embodiments, nucleic acid fragments may be generated from one, two or more mammalian genomes or transcriptomes by polymerase chain reaction (PCR) using, for example, random or degenerate oligonucleotides. Random or degenerate oligonucleotides may include restriction enzyme recognition sequences to allow for cloning of the amplified nucleic acid into an appropriate nucleic acid vector A SEP library may be produced by a method comprising:
(i) producing chosen fragments from nucleic acids from mammalian tissue;
(ii) inserting the nucleic acid fragments into an expression vector adapted to express the fragment; and
(iii) expressing the peptide encoded by the nucleic acid fragment.

In one embodiment, the chosen nucleic acids may be synthesised as described herein.

The nucleic acid fragments may be produced from genomic DNA, cDNA, or amplified nucleic acid from one or more genomes or transcriptomes, preferably genomes, and preferably human genomes. Suitably the nucleic acid fragments are derived from human genomes or transcriptomes.

The nucleic acid fragments may be produced from a mixture of nucleic acids (i.e. genomes or transcriptomes) from different organisms. The nucleic acids may be present in the mixture in an amount that is proportional to the complexity and size of the genome (or transcriptome), for example, in comparison to the complexity and size of other genomes in the mixture. This results in approximately equal representation of the genome fragments.

Nucleic acid fragments may be generated from one or two or more mammalian genomes or transcriptomes by one or more of a variety of methods known to those skilled in the art. Suitable methods include those methods for random cloning, as described above.

Nucleic acid encoding a SEP may be flanked (for example 5' and 3' to the coding sequence) by specific sequence tags. Sequence tags comprise for example 10 to 50 nucleotides of known sequence which may be used as binding sites for oligonucleotide primers. Preferably, the sequence of the tag is not found in the mammalian genome. This allows the coding sequence of a SEP to be conveniently amplified from the mammalian cell, for example by PCR, if required. Suitable automated methods for high-throughput screening, including barcoding and drop-out screens, are described, for example, in Sims et al. *Genome Biology* 2011, 12:R104.

The library of SEPs therefore comprises (i) a plurality of separate and addressable SEPs; or (ii) said library of SEPs expressed from a plurality of separate or addressable nucleic acids that encode SEPs. A library of SEPs may be introduced into a population of mammalian cells by expressing a library of nucleic acids encoding a diverse population of SEPs in said population of mammalian cells.

In one embodiment, the SEP library may comprise $1 \times 10^6$ or $1 \times 10^5$ or more different amino acid sequences or is expressed from a plurality of nucleic acids comprising $1 \times 10^6$ or $1 \times 10^5$ or more different nucleic acid sequences that encode SEPs. Suitably the number of different amino acid or nucleic acid sequences is in the region of $1 \times 10^6$ or $1 \times 10^5$ to $1 \times 10^{10}$ different sequences, such as $1 \times 10^8$ to $1 \times 10^9$ different sequences.

Further libraries could encompass bespoke cloned SEPs from larger human proteins, representing known smaller sub-domains. These will be of similar size to natural SEPs, but are derived from conventionally characterised cDNA sequences.

In preferred embodiments, a population of mammalian cells is transfected or transduced with a library of nucleic acids encoding a diverse population of SEPs. The library may be pooled to allow simultaneous transfection or transduction and screening of all the members of the library.

Once a SEP of interest is identified, e.g. as one which alters the phenotype of a cell, the SEP may be isolated for further analysis as described herein. Techniques for the isolation of nucleic acid from a mammalian cell are well-known in the art. For example, total DNA may be isolated from the cells and the nucleic acid encoding the SEP may then be amplified from the isolated total DNA. In some preferred embodiments, the nucleic acid may be amplified using primers which hybridise to the sequence specific tags flanking the SEP coding sequence.

Nucleic acids encoding SEPs or amplification products thereof may be cloned into vectors and/or sequenced.

In some embodiments, the identified nucleic acids may be further manipulated, for example by re-cloning. In some embodiments, the nucleic acid may be cloned into an expression vector adjacent to another nucleic acid encoding a heterologous peptide, such that the vector expresses a fusion protein comprising the SEP fused to the heterologous peptide. Suitable heterologous peptides include epitope tags, affinity tags and cell penetrating peptides (CPPs).

Various approaches for the production of SEPs are available. Encoding nucleic acid may be expressed to produce the SEP (see for example, Recombinant Gene Expression Protocols Ed R S Tuan (March 1997) Humana Press Inc). Alternatively, SEPs may be generated wholly or partly by chemical synthesis. SEPs may be synthesised using liquid or solid-phase synthesis methods; in solution; or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof. Chemical synthesis of peptides is well-known in the art (J. M. Stewart and J. D. Young, Solid Phase Peptide Synthesis, 2nd edition, Pierce Chemical Company, Rockford, Ill. (1984); M. Bodanzsky and A. Bodanzsky, The Practice of Peptide Synthesis, Springer Verlag, New York (1984); J. H. Jones, The Chemical Synthesis of Peptides. Oxford University Press, Oxford 1991; in Applied Biosystems 430A Users Manual, ABI Inc., Foster City, Calif.; G. A. Grant, (Ed.) Synthetic Peptides, A User's Guide. W. H. Freeman & Co., New York 1992, E. Atherton and R. C. Sheppard, Solid Phase Peptide Synthesis, A Practical Approach. IRL Press 1989 and in G. B. Fields, (Ed.) Solid-Phase Peptide Synthesis (Methods in Enzymology Vol. 289). Academic Press, New York and London 1997).

Phenotypic screens are then used to systematically enumerate the endogenous functional roles for the sequences, such as SEP sequences. In addition to screening naive sORFs as part of SEP libraries and/or SEP libraries, it is also anticipated that diseased cells such as cancer cells may express a different repertoire of sORFs or SEPs than normal, non-diseased cells. Differentially-expressed sORFs or SEPs may form part of the dysregulated signaling pathways seen in diseased cells such as cancer cells, just as microRNA expression profiles are altered in cancer/diseased versus normal cells. These also represent an enriched pool of sORFs or SEPs to screen in phenotypic assays for any diseased state.

In another aspect, there is provided a method of identifying differentially-expressed sORFs or SEPs in diseased cells compared to control cells by exposing a population of in vitro cultured mammalian cells capable of displaying an altered phenotype to a library of said differentially-expressed sORFs or SEPs; identifying a cell in the population that displays an alteration in said phenotype following said exposure; identifying a sORF or SEPs that alters said phenotype of the cell; identifying a test compound that binds to said target protein and competes or blocks binding of said sORF or SEPs, providing said identified test compound.

Methodologies for performing phenotypic screens using SEPs can range from: 1) Pathway-specific readouts that use heterologous reporters (for example GFP or Luciferase) to register either total protein levels, protein localisation or ultimate pathway activity at the level of gene transcription in live cells; 2) Registering endogenous protein levels, or their localisation, using antibodies or other affinity reagents, or pathway-specific transcriptional outputs using qPCR or RNA-sequencing in fixed 'non-living' cells; 3) High-content, or 'holistic' based readouts in live cells that are capable of registering specific 'destination' phenotypic readouts of therapeutic relevance, such as differentiation, senescence and cell-death, all of which are coordinated and can be specifically modulated by a complex interplay of multiple cellular pathways.

In a specific aspect of the invention that covers 'holistic' phenotypic assays, 'Synthetic Lethality' screening is of particular importance. Synthetic Lethality screening is an approach in which targets, for instance cancer targets, and candidate therapeutics are sought that can selectively impact tumour cells versus normal cells by exploiting unpredictable secondary points of weakness, which can occur in tumour cells as they heavily rewire their signaling pathways to support unrestrained cell proliferation. Such screens therefore must be performed in live cells and in an unbiased fashion by suppressing or modulating genes (using CRISPR), mRNA (using RNAi), or protein, or protein conformation (using Protein-i) in the cell and then determining whether a consistent negative impact on the overall growth or survival of a tumour cell type occurs; preferably one that harbours a specific genetic alteration(s) that occurs in a tumour situation versus a normal cell type. These direct 'holistic' cell-viability output based screens are performed using either large panels of genetically characterised tumour cells and normal cells to gain correlative information on tumour genotype-dependent responses, or more efficiently using specifically-engineered cell lines that are isogenic for a chosen mutant versus normal genotype that exists in cancer cells versus normal cells, respectively.

Another aspect of the invention therefore provides a method of identifying a target protein that modulates the phenotype specifically of a diseased mammalian cell, said method comprising exposing in vitro a population of cultured mammalian cells capable of displaying said phenotype, e.g. wherein said cultured cells provide a disease model, to a library of SEPs; identifying in said cell population an alteration in said phenotype following said exposure, selection of said cells undergoing the phenotypic change and identifying a SEP that alters the phenotype of the cell, providing said SEP and identifying the cellular protein that binds to said SEP.

The term modulation may include inhibition, inactivation, suppression or increased expression and activation. The test compound may be a biomolecule which is introduced to the cell by contacting the cell with the biomolecule or by expressing a nucleic acid encoding a SEP in the cell.

When defining sORFs or SEPs that are differentially expressed in diseased tissue versus normal tissue, genome-based techniques are used, such as microarrays and RNA-sequencing modified to score unconventional sORFs or SEPs, to interrogate undruggable targets and pathways, such KRAS, and many other undruggable disease genes selected from genomics databases and literature reports. Phenotypic screens using these naïve and disease-specific sORF (and/or SEP) libraries are performed for candidate pathway modulating activity; initially in the pathways they were first shown to be differentially expressed, if this was a selection criteria used. This could, for example, encompass a transcriptional reporter assay, configured to assess the effect of the sORF (or SEP) on, for example, various K-Ras-activated signaling pathways, including, but not limited to, AP1, Elk1, NF-kappaB and NFAT. Hit sORFs (or SEPs) showing an ability to modulate these pathways are assessed for pathway specificity, by assaying their effect on other pathways, and resulting specific hits assayed for their ability to differentially affect the viability or functioning of disease versus normal cells. In other phenotypic screening formats, sORFs (or SEPs) are screened directly for these final differential disease vs normal biological readouts.

sORFs/SEPs that elicit robust disease relevant responses in the above initial 'phenotypic screening' stage, then enter a second 'target-ID' stage where the physical binding partner within the cell is identified. This is performed by using a method suitable for detecting protein:protein interactions. For example by expressing affinity-tagged versions of SEPs within a human cell, breaking open the cell using standard lysis techniques compatible with maintaining PPIs, isolating the SEPs and endogenous protein binding partners by affinity chromatography and then identifying SEP binding partners by mass spectrometry (potentially with an intervening SDS-PAGE gel separation step). These techniques enable identification of SEP binding partner(s), molecules in the cell that are natural ligands of the SEP. Other similar biochemical affinity pull-down techniques may be used. Any binding partners identified are confirmed as such in orthogonal assays such as immunoprecipitation or mammalian-2-hybrid assays. Confirmed partners are validated as having a role in the cell signaling pathway (e.g. K-Ras pathway) using established cell biology techniques such as over-expression, knockdown by RNAi, gene targeting by CRISPR or a combination of said methods. Those binding partners with a validated role are bona fide targets for the third and final stage of small molecule probe discovery.

In a further aspect of the invention there is provided a method of identifying a protein interaction site on a target protein wherein the target protein modulates the phenotype of a mammalian cell, said method comprising the steps:
  i. exposing a population of in vitro cultured mammalian cells capable of displaying said phenotype to a library of SEPs;
  ii. identifying and selecting out from the larger bulk of non-responding cells, a cell
  in the population which displays an alteration in said phenotype following said exposure;
  iii. identifying a SEP that alters said phenotype of the cell;
  iv. identifying a cellular protein which binds to said SEP, said cellular protein being a target protein which modulates said phenotype of the mammalian cell;
  v. identifying a test compound which binds to said target protein and displaces or blocks binding of said SEP.

This invention further relates to methods of phenotypic screening of SEP libraries to identify SEPs that modulate a disease-associated pathway, identifying binding partners of these SEPs (present in the diseased cell), identifying these binding partners as novel targets for drug discovery and screening for molecules that modulate the novel target to alter disease state or disease progression.

In a further aspect of the invention there is provided a method of identifying differentially-expressed sORFs or SEPs in diseased cells compared to control cells and then exposing a population of in-vitro cultured mammalian cells capable of displaying an altered phenotype to a library of said differentially-expressed sORFs or SEPs; identifying a cell in the population which displays an alteration in said phenotype following said exposure; identifying a sORFs or SEPs that alters said phenotype of the cell; identifying a test compound which binds to said target protein and competes or blocks binding of said sORF or SEP and providing said identified test compound.

The diseased cells are preferably selected from cancer cells, autoreactive T-cells, inflamed cartilage cells and insulin-resistant cells.

One method involves the identification of SEPs which modulate cell-signaling pathways and the identification of surface sites on PPIs on proteins that participate in signal transduction and may be useful as drug targets to modulate cell-signaling pathways, in particular pathways which are active in cancer cells.

A cell signaling pathway is a series of interacting factors in a cell that transmit an intracellular signal within the cell in response to an extracellular stimulus at the cell surface and leading to changes in cell phenotype. Transmission of signals along a cell signaling pathway results in the activation of one or more transcription factors which alter gene expression Preferred cell signaling pathways for SEP screens display aberrant activity in disease models, for example activation, up-regulation or mis-regulation in diseased cells, such a cancer cells. For example a pathway may be constitutively activated (i.e. permanently switched on) in a cancer cell, or inappropriately activated by an extracellular ligand, for example in an inflammatory cell in rheumatoid arthritis.

A functional cell signaling pathway is a pathway that is intact and capable of transmitting signals, if the pathway is switched on or activated, for example by an appropriate extracellular stimulus. An active cell signaling pathway is a pathway that has been switched on, for example by an appropriate extracellular stimulus and is actively transmitting signals.

Suitable cell signaling pathways include any signaling pathway that results in a transcriptional event in response to a signal received by a cell.

Cell signaling pathways for investigation as described herein may include cell signaling pathways that may be activated or altered in cancer cells, such as Ras/Raf, Hedgehog, Fas, Wnt, Akt, ERK, TGFβ, EGF, PDGF, Met, PI3K and Notch signaling pathways.

Following identification of the binding partner of a SEP, the binding site, region or domain of the binding partner that interacts with the SEP may be identified. This site, region or domain may also be useful as a target site for the development of therapeutics that modulate the pathway.

For example, X ray crystallography, NMR or standard biochemical techniques, such as immunoprecipitation, based on series of deletion constructs may be performed. For example, SEPs may be co-crystallised with the target protein and the structure solved.

Following identification of a target protein by a method described herein, the interaction site of the target protein may be investigated. The interaction site is the site or region at which the SEP binds to modulate the activity of the target protein. Since binding at the interaction site modulates activity, the interaction site is the site or region of a target protein through which the target protein binds to a binding partner. For example, the interaction site may be the site of a protein:protein interface when the target protein is bound to its binding partner.

Having identified a SEP that alters a cellular phenotype and produced the SEP, optionally as a fusion protein, a method may further comprise confirming the effect of the SEP on the phenotype of a mammalian cell. For example, SEPs that have been synthesised with a Cell-Penetrating Peptide (CPP) may be used directly on the cells in order to elicit a phenotypic deflection.

Blockade of the interaction site by a SEP that binds at the site may disrupt binding of the target protein to a binding partner. Binding at the interaction site may therefore modulate the activity of the target protein and alter one or more phenotypic traits or characteristics.

The current invention therefore provides a method that allows a high complexity SEP library and/or the full complexity of the 'SEPome' to be screened in high-throughput assays in human cells to: 1) Determine their biological functionality in modulating human disease pathways; 2) Isolate the endogenous cellular target(s) that elicit those phenotypes; and 3) define novel druggable space within those targets, which can then be exploited to design novel small molecule drugs.

In a further aspect of the invention there is therefore provided a binding partner that binds the SEP, which may be identified, said binding partner being a candidate target protein for modulation of a disease-associated pathway.

Inhibitory biomolecules expressed from test nucleic acids identified from a library as described above may be used to screen for intracellular binding partners, for example cellular proteins that bind to the biomolecule. For example, the expressed biomolecule may be used as a bait molecule to identify intracellular binding partners in a mammalian cell or cell extract. Cellular proteins that bind to the bait biomolecule may be isolated.

As described herein, the discovery of small-molecules that recapitulate the binding properties and phenotype of SEPs can be achieved either by crystallisation of the SEP with its binding partner and the resulting interface 3D structure used to inform de novo drug design, or by the generation of competition-based assays (e.g., fluorescent polarisation assays, ELISA, BiaCore or Alpha LISA) to screen in high-throughput small-molecule libraries, in increasing titrations of exposure to the chemical compound, that can displace the SEP:endogenous partner complex. Such small molecules are tested for their ability to recapitulate the phenotype of the original SEP, and optimisation of the shape and binding properties of these small-molecule hits, typically again using x-ray crystallography protein structure-guided techniques.

Conventional techniques, such as displacement assays may be employed, to screen for compounds that compete with the SEP for binding to the target protein. For example, a method may comprise contacting a complex comprising the target protein bound to the SEP with a test compound. Displacement of the SEP by the test compound is indicative that the test compound binds to the target protein at the same site as the SEP. Standard displacement assay platforms, such as Alpha-LISA™ or fluorescence polarisation, may be employed.

SEPs that can displace the test compound from the target protein and/or compounds that can displace the SEP, are predicted to also inhibit the activity of the target protein in a cell, and may be useful in the development of therapeutics.

Methods of the invention may therefore further comprise screening for test compounds, such as small organic molecule, antibodies, nucleic acids or peptides that bind to the same interaction site on a target protein as a SEP identified as described above.

Another aspect of the invention provides a method of screening for a compound capable of blocking or altering the SEP: SEP-partner interaction, in which a compound modulates a disease-associated pathway whereby the compound and the SEP are co-introduced to a population of mammalian cells expressing the SEP-partner, and assaying for modulation of the same disease associated pathway modulated by the SEP: SEP-partner interaction.

Various further aspects and embodiments of the present invention will be apparent to those skilled in the art in view of the present disclosure.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above and tables described below.

EXAMPLES

A) Use of sORF Library-Derived SEPs to Find Novel Phenotype-Associated Targets

To assemble a library of predicted sORFs for expression of SEPs and phenotypic screening of SEPs in human cells, a genome wide search for putative open reading frames of <150 amino acids in size that do not necessarily harbour conventional promoter or gene-regulatory structures was performed, with additional analysis of interspecies conservation as an indicator of non-random occurrence. These candidate sORFs present in the human genome were then cloned into lentiviral expression vectors for SEP expression. Over 2000 putative sORFs were assembled in expression libraries for use in Protein-i based phenotypic screens in human cells.

The library of sORFs was screened against Notch and NF-kappaB signaling in order to identify sORFs active against these therapeutically-important pathways. The methodology of these screens is as follows:

1) NF-kappaB Screen

HEK293FT cells in 96-well plates were transfected with plasmid constructs containing a firefly luciferase gene positioned downstream of a DNA element which is responsive to activation of the NF-kappaB transcription factor, and with a plasmid containing the renilla luciferase gene under the control of a 'housekeeping' DNA element which is not responsive to NF-kappaB. In addition to these reporter constructs, expression plasmids containing peptide-encoding sequences (Protein-i inserts), a subset of which are sORF sequences, were co-transfected. 6 hours after transfection, cells were stimulated by the addition of 1 ng/ml recombinant TNF-alpha, a known activator of the NF-kappaB pathway. Positive (4G9) and negative (CYLD) controls were included. After 24 hours of stimulation, each well was assayed for firefly and renilla luciferase activity using a commercially-available reagent system, and luminescence was read out on a BMG Clariostar plate reader. Data was analysed by normalising the NF-kappaB-dependent firefly luciferase activity to the NF-kappaB-independent renilla luciferase activity. Data emerging from this screen is shown in FIG. 1.

Figure 1:
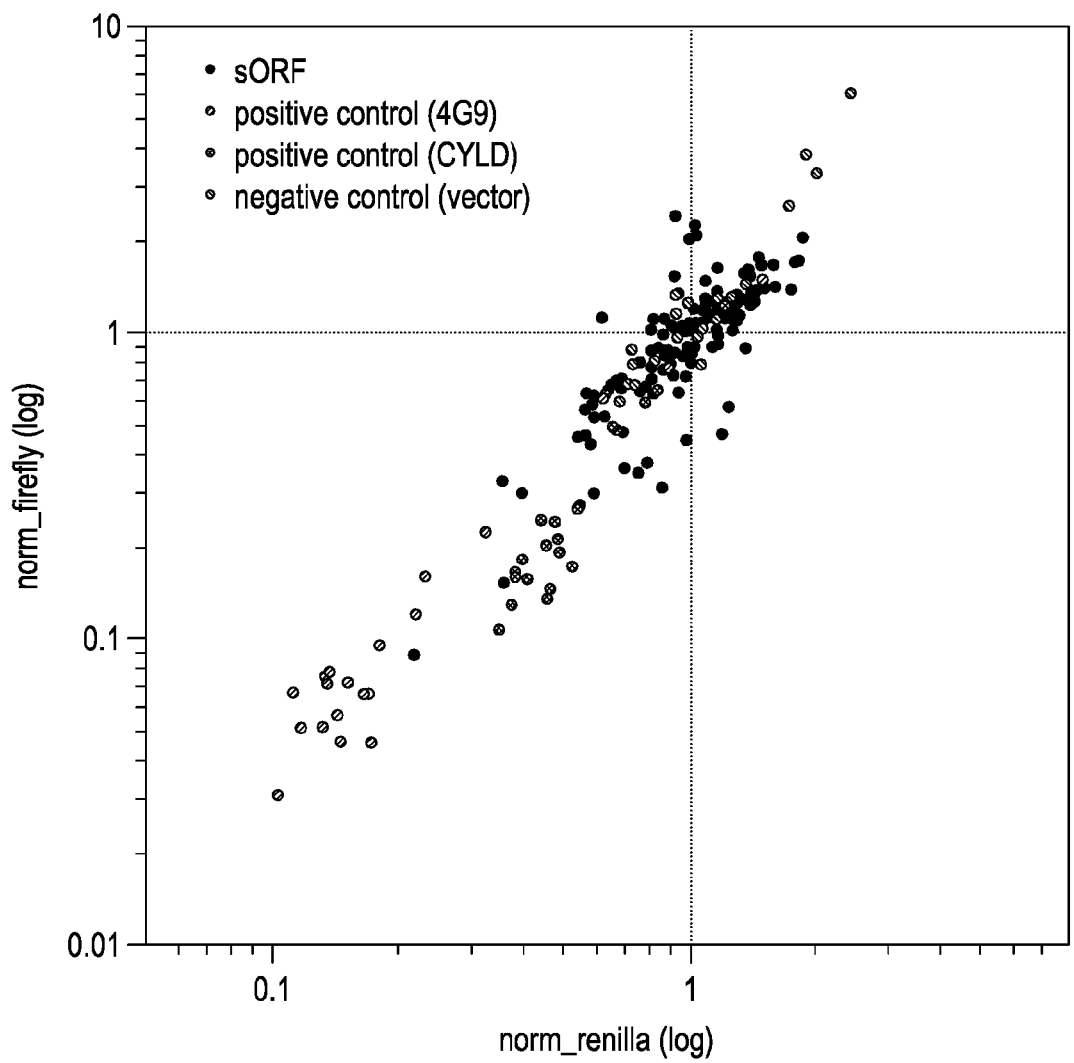
FIG. 1 shows a plot of luminescence from firefly luciferase downstream of an NFkB promoter (i.e. firefly luciferase activity driven by a NFkB transcriptional reporter) and luminescence from renilla luciferase downstream of a control CMV-promoter obtained from a NFkappaB screen. Luciferase activity was read out on a BMG Clariostar plate reader.

FIG. 1 shows that, whilst the vast majority of the sORF library components fail to show any effect upon NF-kappaB signaling, there are several sORF library components which are capable of deflecting the response to TNF-alpha. These sORFs map to the area of the scatter plot characterised by CPLD, a known regulator of NF-kappaB signaling. Of interest is that there are also several putative enhancers of NF-kappaB signaling, suggesting that sORFs might be a rich source of both pathway inhibitors and enhancers.

Figure 2:
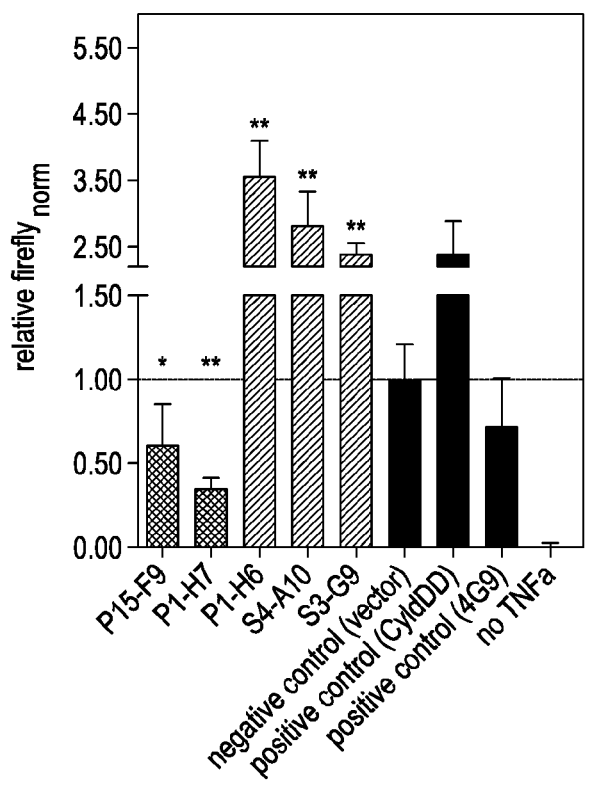
FIG. 2 shows relative luminescence from firefly luciferase obtained from an NFkappaB screen in the presence of a range of SEPs.

Reanalysis of candidate hits from the screen above is shown in FIG. 2 which shows 5 true or validated hits, two of which are sORFs (Prefixed with 'S').

2) Notch Screen

HEK293FT cells in 96-well plates were transfected with plasmid constructs containing a firefly luciferase gene positioned downstream of a DNA element which is responsive to activation of the CBF1 transcription factor, the key downstream target of Notch, and with a plasmid containing the renilla luciferase gene under the control of a 'housekeeping' DNA element which is not responsive to Notch. In addition to these reporter constructs, Notch signaling was activated by co-transfection of a plasmid expressing a constitutively-active form of Notch, namely the Notch intracellular domain or NICD. As for NF-kappaB, peptide-encoding vectors (Protein-i vectors), which include sORFs, were expressed by co-transfection of their expression plasmid. 24 hours after transfection, each well was assayed for firefly and renilla luciferase activity using a commercially-available reagent system, and luminescence was read out on a BMG Clariostar plate reader. Data was analysed by normalising the Notch-dependent firefly luciferase activity to the Notch-independent renilla luciferase activity. Data emerging from this screen is shown in FIG. 3.

Figure 3:
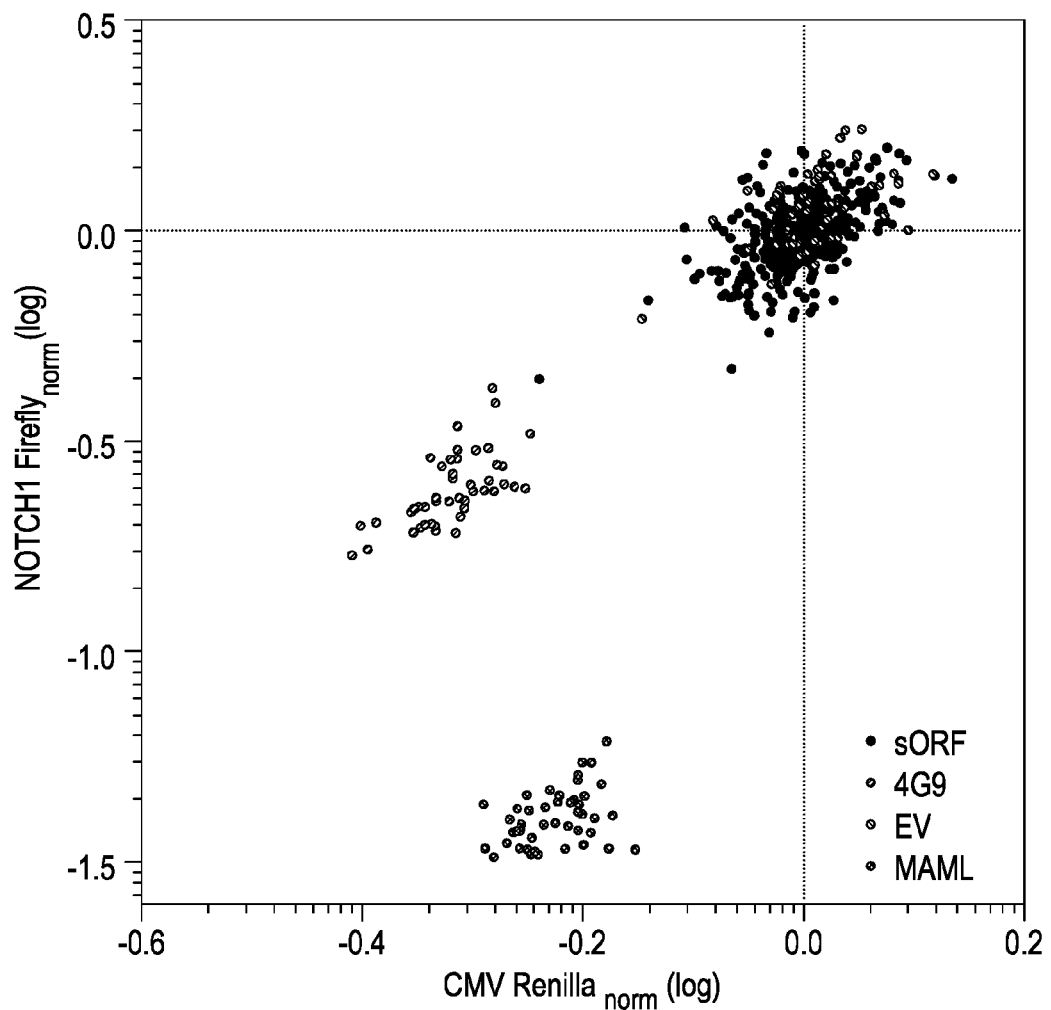
FIG. 3 shows a plot of luminescence from firefly luciferase (downstream of a Notch-responsive promoter) and renilla luciferase (downstream of a control CMV-promoter), activity obtained from a Notch screen read out on a BMG Clariostar plate reader.

As observed for the NF-kappaB screen, FIG. 3 shows that, whilst the vast majority of the sORF library components fail to show any effect upon Notch signaling, there are several sORF library components are capable of deflecting the Notch response. These sORFs tend towards the area of the scatter plot characterised by a dominant negative version of the MAML1 (denoted as MAML), which is a known and very strong ectopic inhibitor of Notch signaling.

Figure 4:
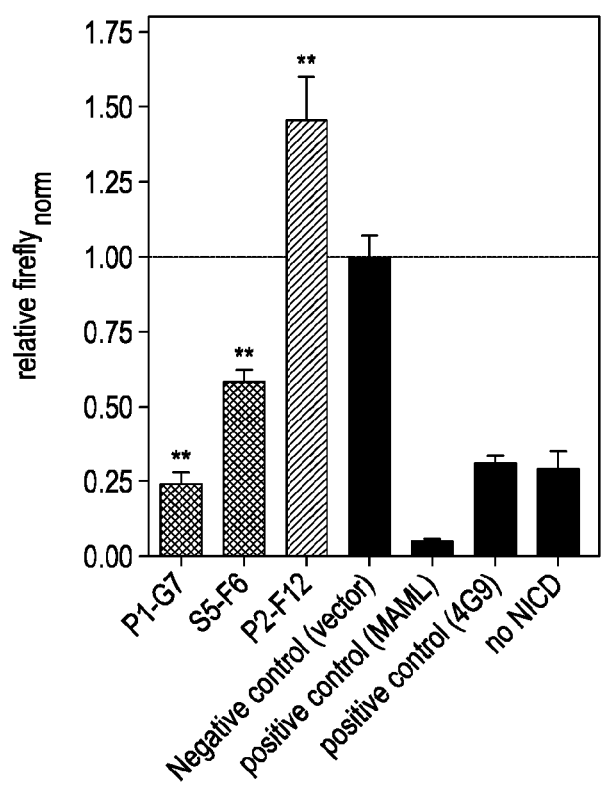
FIG. 4 shows relative luminescence from firefly luciferase obtained from a Notch screen in the presence of a range of SEPs.

Reanalysis of candidate hits from the screen above shows 3 true or validated hits, one of which is a sORF (Prefixed with 'S') (FIG. 4).

B) Use of Bespoke cDNA-Derived SEPs to Find Novel Phenotype-Associated Targets

Using an expression database available from NCBI or UniProt, all the cDNAs, and therefore proteins, expressed in particular human cells is described. The proteome is broken down, bioinformatically, into protein sequences of SEP-like lengths. In this instance, SEPs of 46 amino acids were used. Where possible, protein domains such as those identified by databases, such as Pfam (described for example in Finn et al. Nucleic Acids Research (2014) Database Issue 42:D222- D230) are used to define the boundaries of the cDNA-derived SEPs, such that the final library contains expression clones corresponding to specific, annotated protein domains. Using gene synthesis techniques, sets of 'cDNA-derived SEPs' are generated, and cloned into expression vectors using routine gene cloning techniques. The libraries are used to screen for phenotypic alterations using the assay formats described above, either as pooled or arrayed libraries.

1) Pooled 6-Thioguanine Resistance Screen

Resistance to the chemotherapeutic drug 6-thioguanine has been previously demonstrated to be a fairly strict selection system with a narrow group of proteins being able to mediate the phenotype (see Wang et. al, Science 2014, 343(6166): 80-84 for a comparison). We sought to use this system to demonstrate how SEPs can be utilized in identifying phenotype modulating proteins even under such stringent conditions.

HEK293 cells were transfected with a pooled library of SEPs contained in a lentiviral vector. Virus was harvested, titered, and a batch of KBM7 cells was infected with the SEPs. The library of SEP-transduced cells was subsequently exposed to a concentration of 6-thioguanine that was experimentally determined to kill 99.999% of KBM7 cells. Survivors, carrying inserts of resistance-inducing SEPs were isolated from the pool, expanded and genomic DNA was harvested. The SEPs were amplified using PCR and submitted to Next Generation Sequencing. After bioinformatics analysis of the data, hit SEPs mediating the resistance to 6-thioguanine and likely acting upon mismatch repair processes were identified (FIG. 5).

2) Pooled Hippo Signaling Screen

To measure the activity of the Hippo Signaling pathway we designed a transcriptional reporter for a YAP/TEAD binding element linked to GFP expression. Cells transduced with such a construct will show strong GFP expression if YAP oncogenic signaling is active and low expression of YAP if signaling is inhibited.

As in 1) we transduced a pool of cells with a library of SEPs using lentivirus. The target cell line, HEK293A, has been previously demonstrated to display differential Hippo Signaling dependent on cell density. We plated cells at low density in order to induce YAP activity (and subsequently GFP expression) and used flow cytometry to isolate a population of cells with lower than average expression of GFP and a control population with average expression of GFP. We then submitted both samples to Next Generation Sequencing analysis as in 1). Abundance of SEP sequences in the control set and the YAP-low set were compared and SEPs enriched in the YAP-low set and therefore likely to reduce YAP oncogenic signaling were identified (FIG. 6).

3) Diseased Cell Screen

Libraries of cDNA-derived SEPs are generated using bioinformatics expression profiles from normal or diseased tissues. Those cDNA-derived SEPs which are differentially expressed in, for instance, cancer versus normal tissues, are identified. For example, a library of cDNA-derived SEPs identified as being differentially expressed in pancreatic cancer cells is screened to see if it affects K-Ras-dependent signaling, since K-Ras is the predominant oncogenic driver in this cancer type.

The invention claimed is:

1. A method of identifying a target protein that modulates a phenotype of a mammalian cell, said method comprising:
exposing a population of in vitro cultured mammalian cells capable of displaying said phenotype to a library of short peptides, wherein each short peptide is less than 150 amino acids and is expressed by a nucleic acid, wherein exposing said population of mammalian cells to the library of short peptides comprises expressing a library of nucleic acids encoding a diverse population of short peptides in said population of mammalian cells, and wherein the library of short peptides comprises bespoke short peptides designed in silico;

identifying in said population of mammalian cells an alteration in said phenotype following said exposure;

selecting cells undergoing a phenotypic change and identifying a short peptide of the library of short peptides that alters the phenotype of the selected cells; and providing said short peptide and identifying a cellular protein that binds to said short peptide, said cellular protein being a target protein that modulates the phenotype of the selected cells;

wherein the target protein is not identified prior to exposing the population of mammalian cells to the library of short peptides.

2. The method according to claim 1, wherein the library of short peptides comprises human short peptides.

3. The method according to claim 1, wherein the short peptide is a peptide of 6-130 amino acids.

4. The method according to claim 1, wherein the cellular protein and the short peptide are used in an assay to identify ligands that bind to said cellular protein and disrupt short peptide binding.

5. A method of identifying a compound which binds to a target protein and displaces or blocks binding of a short peptide, wherein the compound modulates a phenotype of a mammalian cell, said method comprising the steps:
   i. exposing a population of in vitro cultured mammalian cells capable of displaying said phenotype to a library of short peptides, wherein each short peptide is less than 150 amino acids and is expressed by a nucleic acid, wherein exposing said population of mammalian cells to the library of short peptides comprises expressing a library of nucleic acids encoding a diverse population of short peptides in said population of mammalian cells, and wherein the library of short peptides comprises bespoke short peptides designed in silico;
   ii. identifying a cell in the population of mammalian cells that displays an alteration in said phenotype following said exposure;
   iii. identifying a short peptide of the library of short peptides that alters said phenotype of the cell;
   iv. identifying a cellular protein that binds to said short peptide, said cellular protein being a target protein that modulates said phenotype of the mammalian cell, wherein the target protein is not identified prior to exposing the population of mammalian cells to the library of short peptides; and
   v. identifying the compound that binds to said target protein and displaces or blocks binding of said short peptide.

6. The method according to claim 1, wherein the phenotype of the selected mammalian cells is associated with a disease-associated pathway.

7. The method according to claim 6, wherein the disease-associated pathway is an activated cell signalling pathway; and/or a disease-associated pathway selected from the group consisting of differentiation, transcriptional activity, protein expression, resistance to infection, permeability, and proliferation.

8. The method according to claim 1, wherein the library of short peptides includes rationally selected fragments from larger proteins.

9. The method according to claim 8, wherein the library of short peptides includes predefined subdomains of mammalian peptides or micropeptides.

10. The method according to claim 8, wherein the library of short peptides includes rationally selected fragments from larger proteins based on bioinformatic predictions of domain structures.

11. The method according to claim 1, wherein the library of short peptides is in silico designed to only use expressed proteins from a proteome consensus database.

12. The method according to claim 1, wherein the short peptides in the library are of constant size.

13. The method according to claim 1, wherein the library of nucleic acids comprises bacterial-derived sequences in combination with non-bacterial sequences.

14. The method according to claim 1, wherein the library of nucleic acids comprises mammalian-derived sequences.

15. The method according to claim 1, wherein the library of nucleic acids comprises short fragments of nucleotide sequences from one or more mammalian nucleic acids cloned into expression vectors.

16. The method according to claim 1, wherein the library of nucleic acids comprises short fragments of nucleotide sequences generated through bioinformatics based design of fragments followed by DNA synthesis.

17. The method according to claim 1, wherein the library of short peptides comprises $1\times10^5$ or more different amino acid sequences.

18. The method according to claim 1, wherein the cellular protein is an intracellular binding partner.

19. The method according to claim 1, wherein the phenotype is cell death.

* * * * *